(12) United States Patent
Hyun

(10) Patent No.: US 8,777,855 B2
(45) Date of Patent: Jul. 15, 2014

(54) ULTRASOUND SYSTEM FOR PROVIDING IMAGE INDICATOR

(75) Inventor: Dong Gyu Hyun, Seoul (KR)

(73) Assignee: Samsung Medison Co., Ltd., Hongcheon-gun, Gangwon-Do (KR)

( * ) Notice: Subject to any disclaimer, the term of this patent is extended or adjusted under 35 U.S.C. 154(b) by 0 days.

(21) Appl. No.: 13/403,556

(22) Filed: Feb. 23, 2012

(65) Prior Publication Data

US 2012/0220873 A1 Aug. 30, 2012

(30) Foreign Application Priority Data

Feb. 24, 2011 (KR) .................. 10-2011-0016701
Feb. 15, 2012 (KR) .................. 10-2012-0015193

(51) Int. Cl.

| A61B 8/14 | (2006.01) |
|---|---|
| A61B 5/06 | (2006.01) |
| A61B 8/00 | (2006.01) |
| A61B 8/08 | (2006.01) |
| A61B 6/00 | (2006.01) |

(52) U.S. Cl.
CPC . *A61B 5/06* (2013.01); *A61B 8/463* (2013.01); *A61B 8/5238* (2013.01); *A61B 6/5247* (2013.01); *A61B 8/00* (2013.01)
USPC ............................ 600/437; 600/443; 382/131

(58) Field of Classification Search
CPC ........ A61B 5/06; A61B 8/463; A61B 8/5238; A61B 6/5247; A61B 8/00
USPC .................................. 600/437, 443; 382/131
See application file for complete search history.

(56) References Cited

U.S. PATENT DOCUMENTS

| 5,211,167 A | 5/1993 | Amenomori |
|---|---|---|
| 2002/0138007 A1 | 9/2002 | Nguyen-Dinh et al. |
| 2004/0019270 A1 | 1/2004 | Takeuchi |
| 2005/0119569 A1* | 6/2005 | Ohtake ..................... 600/437 |
| 2005/0203417 A1 | 9/2005 | Okuno |
| 2006/0058654 A1 | 3/2006 | Di Marco et al. |

(Continued)

FOREIGN PATENT DOCUMENTS

| JP | 2010-119625 A | 6/2010 |
|---|---|---|
| KR | 10-2010-0087521 | 8/2010 |

OTHER PUBLICATIONS

European Search Report issued in European Patent Application No. 12156279.7 dated Jul. 2, 2012.

(Continued)

*Primary Examiner* — Baisakhi Roy
(74) *Attorney, Agent, or Firm* — McDermott Will & Emery LLP

(57) ABSTRACT

Embodiments of an ultrasound system for outputting an ultrasound image through an ultrasound examination are disclosed. In one embodiment, an ultrasound system comprises an ultrasound probe, a sensor unit, a processor unit and an input unit. The ultrasound probe transmits and receives an ultrasound beam to and from the examination portion of a target object. The sensor unit is disposed in the ultrasound probe and detects a posture and/or a position of the ultrasound probe to form posture information and/or position information of the ultrasound probe. The processor unit moves an image indicator corresponding to the posture information and/or the position information. The image indicator includes an ultrasound beam direction marker that is indicative of a transmission direction of the ultrasound beam transmitted from the ultrasound probe to the target object. The input unit is configured to control the processor unit.

11 Claims, 6 Drawing Sheets

(56) References Cited

U.S. PATENT DOCUMENTS

| | | | |
|---|---|---|---|
| 2007/0073148 A1* | 3/2007 | Kim | 600/437 |
| 2008/0009724 A1* | 1/2008 | Lee et al. | 600/437 |
| 2009/0036775 A1* | 2/2009 | Ikuma et al. | 600/443 |
| 2010/0191114 A1 | 7/2010 | Hyun et al. | |
| 2010/0239150 A1* | 9/2010 | Ishikawa et al. | 382/131 |
| 2010/0298705 A1* | 11/2010 | Pelissier et al. | 600/443 |
| 2011/0125020 A1* | 5/2011 | Kondou | 600/443 |

OTHER PUBLICATIONS

Korean Office Action with English translation issued in Korean Application No. 10-2012-0015193 dated Jul. 1, 2013.

Korean Notice of Allowance issued in Korean Application No. 10-2012-0015193 dated Feb. 26, 2014, w/English translation.

* cited by examiner

| TARGET OBJECT | EXAMINATION POSITION | TARGET ORGAN MARKER | BODY AXIS MARKER | ULTRASOUND BEAM DIRECTION MARKER |
|---|---|---|---|---|
| UTERUS | WALL OF UTERUS |  |  |  |
| ⋮ | ⋮ | ⋮ | ⋮ | ⋮ |

ULTRASOUND SYSTEM FOR PROVIDING IMAGE INDICATOR

CROSS-REFERENCE TO RELATED APPLICATIONS

This application claims priority from Korean Patent Application No. 10-2011-0016701 filed on Feb. 24, 2011 and Korean Patent Application No. 10-2012-0015193 filed on Feb. 15, 2012, the entire disclosures of which are incorporated herein by reference.

TECHNICAL FIELD

The present disclosure relates to an ultrasound system, and more particularly to an ultrasound system automatically providing an image indicator.

BACKGROUND

An ultrasound system has been widely used in the medical image field due to its non-invasiveness and non-destructiveness to a target object. The ultrasound system outputs an ultrasound image of an examination portion of the target object by means of an image display device. Since the ultrasound image generally shows only a part of the target object, it may be difficult for an operator to intuitively recognize types of the target object and directions of probing the target object. As a solution coping with this difficulty, an image indicator (which may be referred to as a body marker) indicative of the types of the target object may be displayed in the image display device along with an ultrasound image. The image indicator may be represented as texts or an icon similar to a shape of the target object.

With the ultrasound system wherein the image indicator is displayed as texts, there is an inconvenience since the operator must directly input the texts representing the image indicator such that the target object is associated with the image indicator. Further, as for the ultrasound system wherein the image indicator is displayed as an icon, such icon merely shows the type of the target object and fails to indicate any information on the directions of probing the target object.

SUMMARY

Embodiments of an ultrasound system for acquiring an ultrasound image of an examination portion of a target object are provided. In one embodiment, by way of non-limiting example, an ultrasound system comprises an ultrasound probe, a sensor unit, a processor unit and an input unit. The ultrasound probe is configured to transmit and receive an ultrasound beam to and from the examination portion of the target object. The sensor unit is disposed in the ultrasound probe and configured to detect a posture and/or a position of the ultrasound probe to form posture information and/or position information of the ultrasound probe. The processor unit is configured to move an image indicator corresponding to the posture information and/or the position information. The image indicator includes an ultrasound beam direction marker that is indicative of a transmission direction of the ultrasound beam transmitted from the ultrasound probe to the target object. The input unit is configured to control the processor unit.

This Summary is provided to introduce a selection of concepts in a simplified form that are further described below in the detailed description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments may readily suggest themselves to such skilled persons having the benefit of this disclosure.

Figure 1:
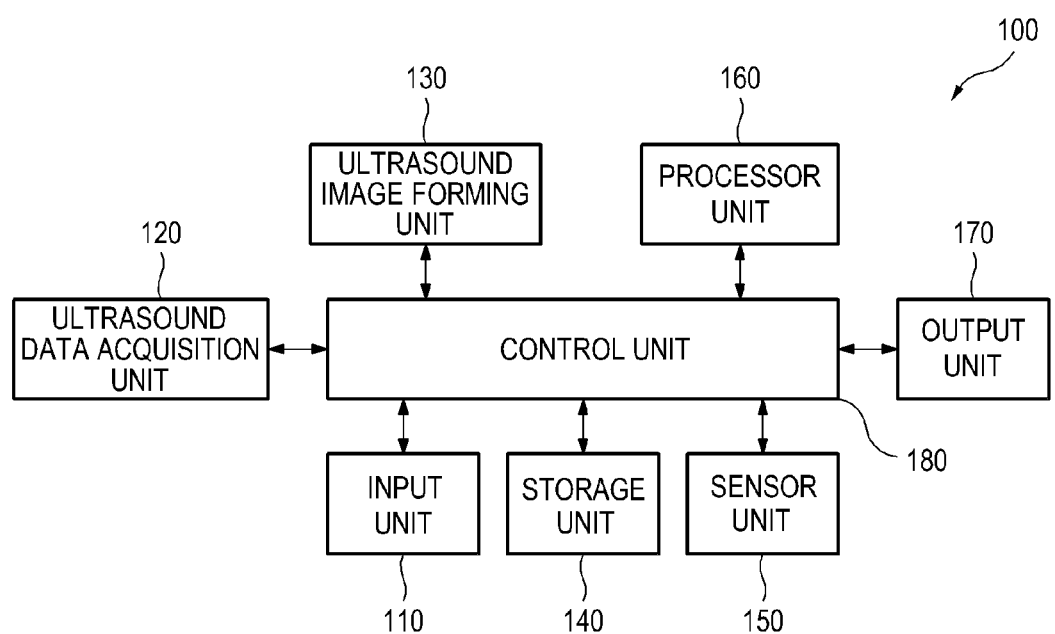
FIG. 1 is a block diagram showing an illustrative embodiment of an ultrasound system according to one embodiment of the present disclosure.
Figure 2:
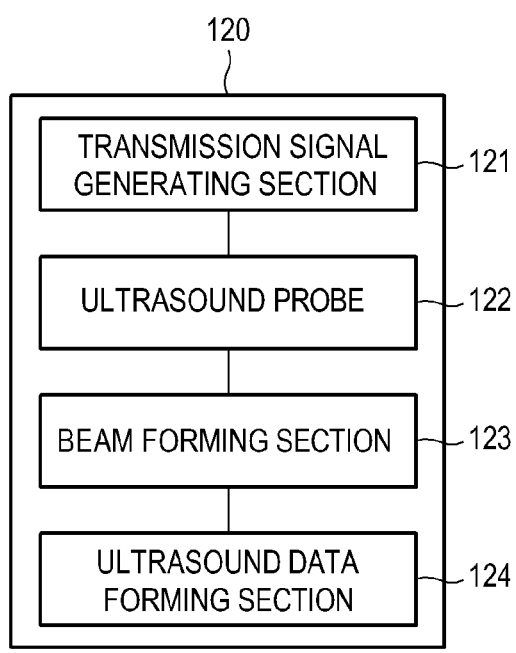
FIG. 2 is a block diagram showing an illustrative embodiment of an ultrasound data acquisition unit according to one embodiment of the present disclosure.
Figure 3:
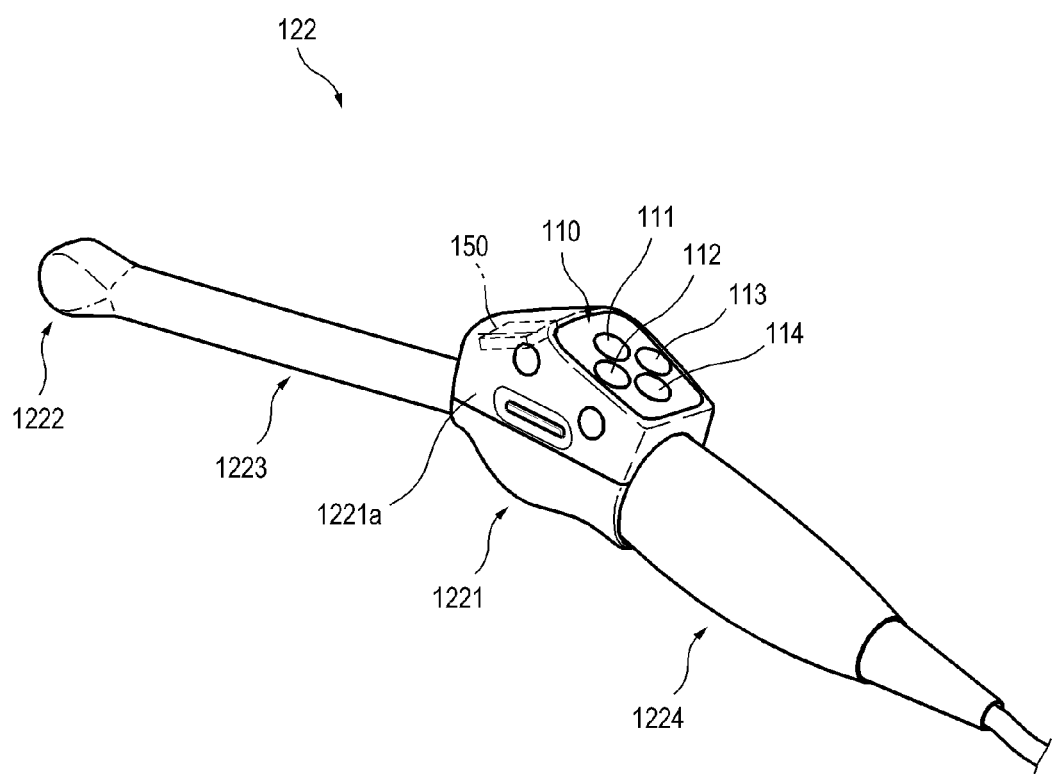
FIG. 3 is a perspective view showing an illustrative embodiment of an ultrasound probe according to one embodiment of the present disclosure.

Referring to FIGS. 1 to 3, an ultrasound system 100, which is constructed in accordance with one embodiment, comprises an input unit 110, an ultrasound data acquisition unit 120, an ultrasound image forming unit 130, a storage unit 140, a sensor unit 150, a processor unit 160, an output unit 170 and a control unit 180.

The input unit 110 is disposed at an ultrasound probe 122. The input unit 110 may be detachably mounted to the ultrasound probe 122. The input unit 110 functions to control the processor unit 160. Since the input unit 110 is provided at the ultrasound probe 122, an operator can easily operate the input unit 110 while performing an examination for a target object by means of the ultrasound probe 122. The operator can input a demand for showing or hiding an image indicator through the input unit 110.

The ultrasound data acquisition unit 120 transmits an ultrasound signal to the target object and receives an ultrasound signal (i.e., an ultrasound echo signal) reflecting from the target object and thus acquires an ultrasound data.

As shown in FIG. 2, the ultrasound date acquisition unit 120 comprises a transmission signal generating section 121, the ultrasound probe 122, a beam forming section 123 and an ultrasound data forming section 124.

The transmission signal generating section 121 generates transmission signals, which are applied to respective transducer elements (not shown), considering positions and focal points of the transducer elements provided in the ultrasound probe 122. In this embodiment, the transmission signal may include a transmission signal for acquiring a frame of an ultrasound image.

The ultrasound probe 122 converts the transmission signal from the transmission signal generating section 121 into an ultrasound signal and then transmits the ultrasound signal to the target object. The ultrasound probe 122 transmits an ultrasound beam, which is formed by a plurality of the transducer elements and comprises a group of the ultrasound signals, to the examination portion of the target object. Further, the ultrasound probe 122 receives an ultrasound echo signal reflecting from the target object and forms an electrical receive signal from the ultrasound echo signal. In this embodiment, the ultrasound probe 122 includes a probe with a probing section, which is configured to be inserted into the uterus through the vagina for purposes of examining the uterus.

As shown in FIG. 3, the ultrasound probe 122 includes an operating portion 1221 and a probing portion 1222. The operating portion 1221 includes a case 1221a that houses or contains parts related to an operation of the ultrasound probe 122. The case 1221a is configured to mount the input unit 110 on one side thereof. In one embodiment, the input unit 110 may be mounted to the case 1221a so as to appear on the side of the case 1221a. In other embodiment, the input unit 110 may be attached to a surface of the case 1221a. In another embodiment, the ultrasound probe may be configured such that the input unit 110 and the operating portion 1221 are integrated with each other and only a portion (e.g., buttons for input) of the input unit 110 appears on a surface of the case 1221a. The ultrasound probe 122 has an elongated cylindrical insertion portion 1223 extending from the case 1221a. The probing portion 1222 is provided at a leading end of the insertion portion 1223. The probing portion 1222 contains a plurality of the transducer elements therein. The ultrasound probe 122 transmits the ultrasound signal to the target object through the transducer elements of the probing portion 1222 and receives the ultrasound echo signal reflecting from the target object through the transducer elements. The ultrasound probe 122 has a grip portion 1224 extending from the case 1221a in a direction opposite to the insertion portion 1223. The grip portion 1224 is a part, which the operator grasps when performing the ultrasound examination with the ultrasound probe 122. The operator can manipulate the input unit 110 by one of his fingers while grasping the grip portion 1224 with his hand. In other embodiment, the ultrasound probe 122 may be configured to pivot the transducer elements in the probing portion 1222 in a predetermined angular range. In such an example, a portion of a drive mechanism for pivoting the transducer elements may be positioned in the grip portion 1224.

The beam forming section 123 converts electrical analog receive signals provided from the ultrasound probe 122 into digital signals. The beam forming section 123 applies delays to the electrical receive signals, which are converted to digital signals, considering the positions and the focal points of the transducer elements. Further, the beam forming section 123 sums the delayed electrical receive signals and outputs a plurality of receive-focused beams.

The ultrasound data forming section 124 forms an ultrasound data by using the receive-focused beams provided from the beam forming section 123. The ultrasound data forming section 124 may perform various signal processes (e.g., gain adjustment, filtering and the like) upon the receive-focused beams provided from the beam forming section 123.

The ultrasound image forming unit 130 forms an ultrasound image by using the ultrasound data provided from the ultrasound acquisition unit 120. The ultrasound image may include the following: a brightness-mode (B-mode) image formed by using reflection coefficients of ultrasound echo signals reflecting from the target object; a Doppler-mode (D-mode) image showing a velocity of a moving object as a Doppler spectrum by means of the Doppler Effect; a color-mode (C-mode) image showing a velocity of a moving object by using predetermined colors mapped to each velocity; and an elastic-mode image showing mechanical characteristics of tissues based on strain representing deformation of the tissues caused by compression.

Figure 5:
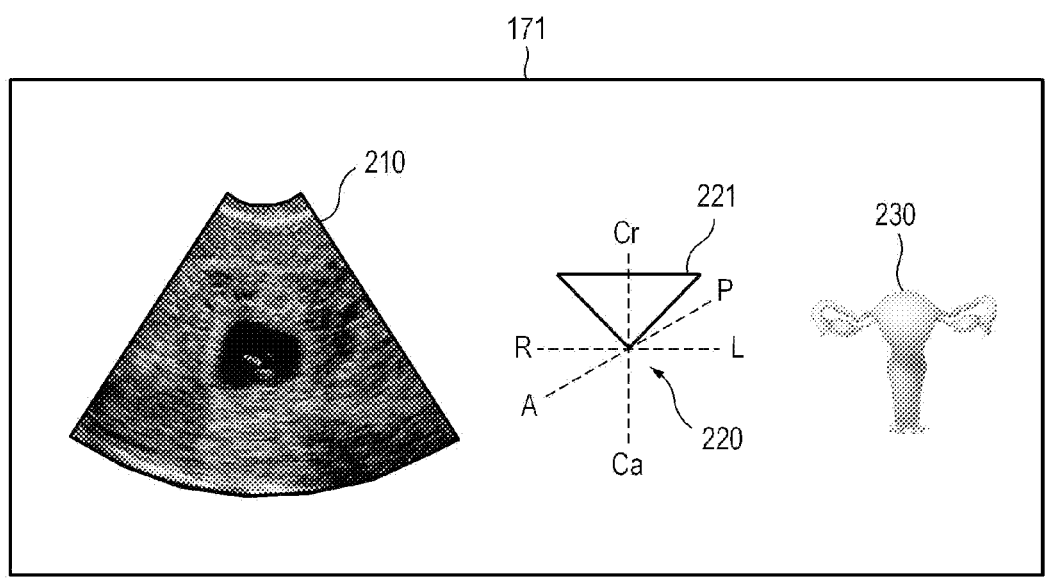
FIG. 5 shows examples of an ultrasound image and an image indicator displayed together with the ultrasound image according to one embodiment of the present disclosure.

The ultrasound image formed by the ultrasound image forming unit 130 is outputted through the output unit 170. The output unit 170 may include a CRT monitor or a flat panel display device. The output unit 170 displays the ultrasound image on its screen 171, as shown in FIG. 5. Further, the output unit 170 displays the image indicator processed by the processor unit 160 together with the ultrasound image.

Figure 4:
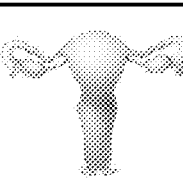
FIG. 4 shows an example of a mapping table for associating a target object, an examination portion and image indicators with one another according to one embodiment of the present disclosure.
Figure 4:
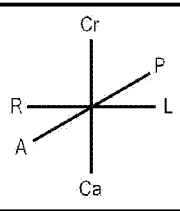
Figure 4:
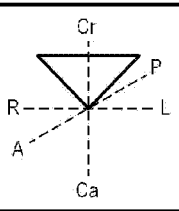

The storage unit 140 stores information or data related to the predetermined image indicators corresponding to a plurality of target objects and examination portions, respectively. In this embodiment, the image indicator includes: a target organ marker 230; a body axis marker 220; and an ultrasound beam direction marker 221, as shown in FIG. 4. The target organ marker 230 indicates a type of the target object such as a heart, a liver, a stomach, a uterus, an anus, etc. The body axis marker 220 indicates an anatomical position of each target object, such as cardinal (Cr), caudal (Ca), anterior (A), posterior (P), right (R) and left (L) by using a three-dimensional coordinate system. The ultrasound beam direction marker 221 indicates a transmission direction of the ultrasound beam transmitted from the ultrasound probe 122 by means of a triangle. In one embodiment, the ultrasound beam direction marker 221 may be displayed along with the body axis marker 220 with an apex of its triangle located at an origin point of the coordinate system of the body axis marker 220. The storage unit 140 stores the above-described image indicators in association with the respective target object and examination portion. By way of example, the storage unit 140 stores the image indicator, which includes the target organ marker 230, the body axis marker 220 and the ultrasound beam direction marker 221, corresponding to the target object and the examination portion as shown by a mapping table of FIG. 4. In this embodiment, the target organ marker and the body axis marker are three-dimensionally represented by using a three-dimensional coordinate system. In other embodiment using a two-dimensional coordinate system, the target organ marker and the body axis marker may be two-dimensionally represented.

The sensor unit 150 is disposed in the ultrasound probe 122. The sensor unit 150 is disposed in the case 1221a of the ultrasound probe 122. The sensor unit 150 detects a posture and a position of the ultrasound probe 122 and forms posture information and position information. The sensor unit 150 may include, but is not limited to, an angular velocity sensor, a magnetic sensor, an accelerometer sensor, a gravity sensor, a gyro sensor, etc. The sensor unit 150 may include any sensor as long as it is capable of sensing 3-dimensional posture and position of the ultrasound probe 122. In another embodiment, the sensor unit 150 may be disposed in the input unit 110.

Figure 6:
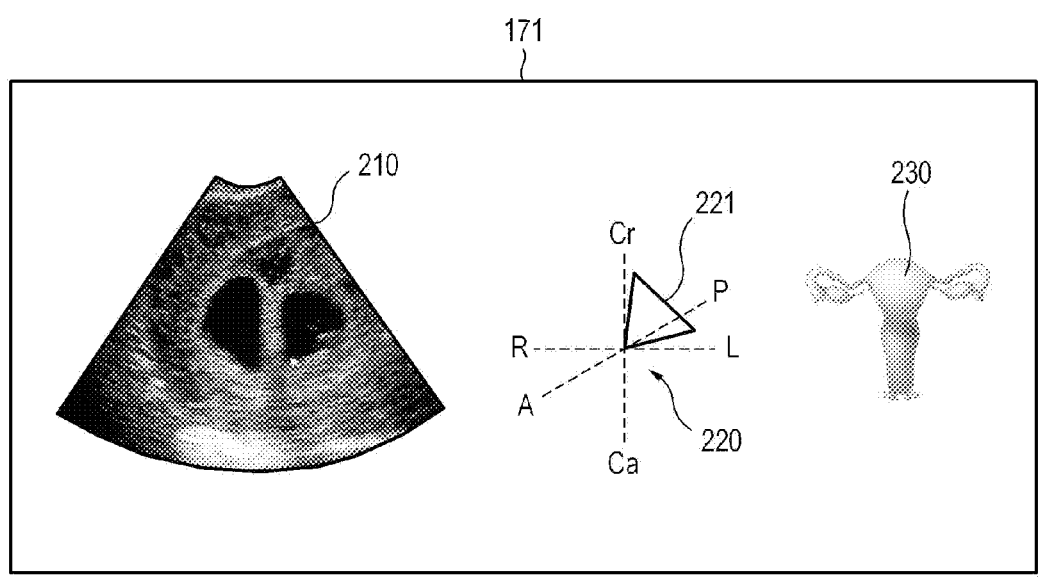
FIG. 6 shows the ultrasound image and the image indicator, which are changed from those in case of an examination state shown in FIG. 5 according to one embodiment of the present disclosure.

The control unit 180 receives signals or commands from each unit and controls each unit according to such signals or commands. In one embodiment, the control unit 180 may be disposed in a main body of the ultrasound system 100. The control unit 180 is configured to output through the output unit 170 the ultrasound image formed by the ultrasound image forming unit 130 and the image indicators 230, 220, 221 processed by the processor unit 160. Further, the control unit 180 is configured to output the ultrasound image, which changes during ultrasound examination, and the image indicator, which changes during ultrasound examination and is processed by the processor unit 160 accordingly. Further-more, the control unit 180 is configured to output the ultrasound image that changes or moves in association with the change or movement of the image indicator. By way of example, as shown in FIG. 5, the ultrasound image 210 and the image indicators 230, 220, 221 at one time point during ultrasound examination may be displayed on the screen 171 of the output unit 170. Further, as shown in FIG. 6, the ultrasound image 210 and the image indicators 230, 220, 221, which change from the state shown in FIG. 5, may be displayed on the screen 171.

The processor unit 160 processes a position, an orientation, etc. of the image indicators 230, 220, 221 based on the posture information and/or the position information of the ultrasound probe 122 formed by the sensor unit 150 and sends them to the control unit 180. Further, the processor unit 160 receives from the sensor unit 150 the posture information and/or the position information of the ultrasound probe 122, which change during ultrasound examination, and performs the process for moving (e.g., rotating, zooming in, zooming out, etc.) the image indicators 230, 220, 221 based on the changing position information and posture information. As such, the sensor unit 150 disposed in the ultrasound probe 122 forms the position information and the posture information of the ultrasound probe 122 and the processor unit 160 moves the image indicators 230, 220, 221 based on the position information and the posture information. Thus, the ultrasound system 100 according to one embodiment can display not only the changing ultrasound image of the examination portion, but also the image indicator associated with the examination portion, while changing them corresponding to the examination state during ultrasound examination. That is, the ultrasound system 100 according to one embodiment can automatically provide the ultrasound image of the examination portion as well as the image indicators associated with the examination portion during ultrasound examination. Further, the ultrasound system 100 according to one embodiment can change or move the ultrasound image according to the change or movement of the image indicators during ultrasound examination.

The input unit 110 disposed in the ultrasound probe 122 is configured to control the processor unit 160. In this embodiment, the input unit 110 is configured to control the processor unit 160 by means of button input. The input unit 110 may include, for example, the following: a button for input related to the process of the image indicator; a button for input related to storage and selection of the information of the ultrasound image and the image indicator; and a button for input related to the operations of the ultrasound probe 122 and/or the units disposed in the ultrasound probe 122. In this embodiment, the input unit 110 includes an initialization button 111, an image selection button 112, a freeze/unfreeze button 113 and an on/off button 114.

In one embodiment, the position of the ultrasound probe 122 may be represented by coordinates (x, y, z) on a three-dimensional Cartesian coordinate system. For example, the Z-axis may correspond to a direction facing the center of the earth and the X-Y plane defined by the X-axis and the Y-axis may be perpendicular to the Z-axis. Further, the X-axis, Y-axis and Z-axis may correspond to an A-P axis, an R-L axis and a Cr—Ca axis shown in FIGS. 5 and 6, respectively. The posture of the ultrasound probe 122 may be represented by three angles ($\theta_x$, $\theta_y$, $\theta_z$) such as Roll, Pitch and Yaw. Roll may refer to rotation around the X-axis in the Y-Z plane. Pitch may refer to rotation around the Y-axis in the X-Z plane. Yaw may refer to rotation around the Z-axis in the X-Y plane.

The initialization button 111 generates a signal for setting a reference state (including a reference posture and a reference position) of the ultrasound probe 122. When the operator presses the initialization button 111 while the ultrasound probe 122 is positioned in the target object for ultrasound examination, the processor unit 160 sets the posture and the position of the ultrasound probe 122 at the time of pressing the initialization button 111 as the reference posture and the reference position of the ultrasound probe 122. The set reference posture and reference position are stored in the storage unit 140. Thus, the posture information and the position information of the ultrasound probe 122, which are detected and formed by the sensor unit 150 at the time of pressing the initialization button 111, may be set as the reference posture and the reference position. In this embodiment, when the operator presses the initialization button 111, the reference position is set by positioning an origin point of the coordinate system to a center of gravity of the ultrasound probe 122 and the reference posture is set by the angles ($\theta_x$, $\theta_y$, $\theta_z$) in the orientation of the ultrasound probe 122 to the origin point.

The image selection button 112 generates signals for selecting the ultrasound image, the body axis marker 220 and the ultrasound beam direction marker 221 while the ultrasound probe 122 performs the ultrasound examination. When the operator presses the image selection button 112 while the ultrasound probe 122 probes the target object, the ultrasound image, the body axis marker 220 and the ultrasound beam direction marker 221 at the time of pressing the image selection button 112 are stored in the storage unit 140.

The freeze/unfreeze button 113 generates signals for freezing or unfreezing the ultrasound image while the ultrasound probe 122 performs the ultrasound examination. When the operator presses the freeze/unfreeze button 113 one time, a still ultrasound image of the target object, which is being probed by the ultrasound probe 122, may be displayed. In such a state, the operator may select, by the image selection button 112, whether to store the body axis marker 220 or the ultrasound beam direction marker 221 in the storage unit 140 together with the still ultrasound image or not. When the operator presses the freeze/unfreeze button 113 one more time, the still ultrasound image is unfrozen and then the ultrasound image of the target object under probing by the ultrasound probe 122 may be displayed.

The on/off button 114 is capable of turning on/off the ultrasound probe 122 by cutting off an electric power supplied to the ultrasound probe 122. Alternatively, when the input unit 110 includes a plurality of the on/off buttons 114, the on/off buttons 114 may be capable of turning on/off the ultrasound probe 122, the sensor unit 150 and the input unit 110.

After the ultrasound probe 122 is moved or rotated from the reference posture and the reference position, the processor unit 160 processes the position and the orientation of the image indicator according to the changed position and posture of the ultrasound probe 122. The sensor unit 150 detects a relative posture and a relative position of the ultrasound probe 122 with respect to the reference posture and the reference position and forms the posture information and the position information associated with the relative posture and position. In this case, the position of the ultrasound probe 122 may be represented by the relative coordinates (x, y, z) with respect to the reference position, and the posture of the ultrasound probe 122 may be represented by the angles ($\theta_x$, $\theta_y$, $\theta_z$) in the orientation of the ultrasound probe 122 at the relative coordinates (x, y, z). The processor unit 160 synchronizes the posture information and the position information formed from the sensor unit 150 with the target organ marker 230 and the ultrasound beam direction marker 221, and then changes the target organ marker 230 and the ultrasound beam direction marker 221 according to the movement or rotation of the ultrasound probe 122, as shown in FIG. 6. That is, the ultrasound beam direction marker 221 moves corresponding to the movement or rotation of the ultrasound probe 122. Thus, the operator can easily recognize the probing direction and the position of the ultrasound image 210. Further, since the ultrasound image 210 may be stored in the storage unit 140 together with the body axis marker 220 and the ultrasound beam direction marker 221 at any time point during the ultrasound examination, the operator can easily recognize a positional relationship of the ultrasound image 210. In particular, when examining the organ, such as the uterus, which has difficulties in distinguishing the left and the right thereof by only the ultrasound image, the operator can easily recognize that the ultrasound image displayed on the screen 171 represents which one of the left and right of the uterus by the automatically-provided ultrasound beam direction marker 221.

Although embodiments have been described with reference to a number of illustrative embodiments thereof, it should be understood that various other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system for outputting an ultrasound image through an ultrasound examination, comprising:
    an ultrasound probe configured to transmit an ultrasound beam to a target object and receive an ultrasound echo signal therefrom;
    a sensor disposed in the ultrasound probe, the sensor being configured to detect a posture and/or a position of the ultrasound probe and forming a posture information and/or a position information of the ultrasound probe;
    a processor configured to move an image indicator based on the posture information and/or the position information, the image indicator including an ultrasound beam direction marker indicative of a direction of the ultrasound beam; and
    an input configured to control the processor,
    wherein the input includes an initialization button, and
    wherein the processor is further configured to set the current posture and/or the current position of the ultrasound probe as a reference posture and/or a reference position, respectively, when the initialization button is operated.

2. The ultrasound system of claim 1, wherein the sensor is further configured to detect a relative posture and/or a relative position of the ultrasound probe with respect to the reference posture and/or the reference position as the ultrasound probe is moved, and
    wherein the processor is further configured to move the image indicator based on the relative posture and/or the relative position.

3. The ultrasound system of claim 2, wherein the ultrasound image is changed in association with a movement of the image indicator.

4. The ultrasound system of claim 1, further comprising a storage,
    wherein the input includes an image selection button and the ultrasound image and the image indicator are stored in the storage when the image selection button is operated.

5. The ultrasound system of claim 1, wherein the input unit includes a freeze/unfreeze button for selecting a still image of the ultrasound image and the image indicator.

6. The ultrasound system of claim 1, wherein the image indicator further includes a body axis marker indicative of an anatomical position of the target object.

7. The ultrasound system of claim 1, wherein the image indicator further includes a target organ maker indicative of a type of the target object.

8. The ultrasound system of claim 1, wherein the processor unit is further configured to move the image indicator three-dimensionally.

9. The ultrasound system of claim 1, wherein the input is disposed at the ultrasound probe.

10. The ultrasound system of claim 9, wherein the input is detachably mounted to the ultrasound probe.

11. The ultrasound system of claim 9, wherein the ultrasound probe includes an operating portion, an insertion portion extending from the operating portion and a probing portion provided at a leading end of the insertion portion, and
    wherein the input is mounted to the operating portion.

* * * * *